Figure 1:
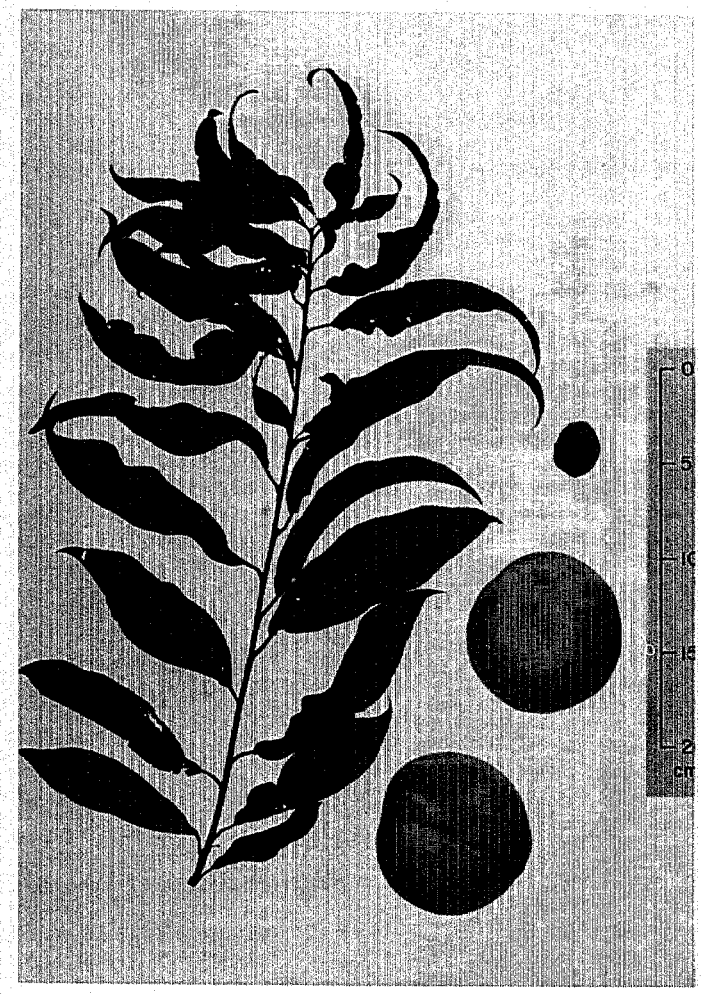

US00PP08394P

United States Patent [19]

Beutel et al.

[11] Patent Number: Plant 8,394

[45] Date of Patent: Sep. 28, 1993

[54] CLINGSTONE PEACH TREE 'RIZZI'

[75] Inventors: James A. Beutel, Davis; James F. Doyle, Clovis; Robert E. Fenton, Big Bear Lake; James T. Yeager, Davis, all of Calif.

[73] Assignee: The Regents of the University of California, Oakland, Calif.

[21] Appl. No.: 966,218

[22] Filed: Oct. 26, 1992

[51] Int. Cl.[5] ..... A01H 5/00

[52] U.S. Cl. ..... Plt./43.1

[58] Field of Search ..... Plt./43.1

*Primary Examiner*—James R. Feyrer
*Assistant Examiner*—Elizabeth C. Kemmerer
*Attorney, Agent, or Firm*—Townsend and Townsend Khourie and Crew

[57] ABSTRACT

A high quality canning clingstone peach in the late maturity group which ripens between the 'Ross' and 'Dr. Davis' varieties and has an extended storage life after harvest and prior to processing.

1 Drawing Sheet

DESCRIPTION

This invention relates to a new clingstone peach variety and more particularly a high quality canning clingstone peach of the late maturity type.

The new variety, originally designated as selection 19, 2-72 and now named 'Rizzi' resulted from an open-pollinated seed of the cling peach cultivar called 'Everts'. Seed of 'Everts' was collected at the University of California facility at Davis, Calif. by Robert Fenton in 1973. The seed was planted in the Pomology nursery at Davis in 1974, and the resultant seedling trees were planted in the permanent seedling block (Block 19) located at the University's Wolfskill Experimental Orchard, Winters, Calif. in the spring of 1975.

In the Drawings

FIG. 1 shows a branch and two fruit typical of the new variety. One fruit depicts the apical aspect and the other depicts the basal aspect. Also shown in the drawing is a clean pit with clinging flesh removed.

The seedling trees of 'Rizzi' first bore fruit in 1978, and were processed that same year. Canned samples of the new variety were shown in January of 1979 at the Canners League of California Annual Fruit Sample Cutting at San Francisco, Calif. The variety was asexually reproduced by grafting budwood into both the "20 Block" at the Experimental Orchard and into the "R Block" at Davis in 1979.

'Rizzi' ripens in mid-August approximately between the 'Ross' and 'Dr. Davis' varieties. It is capable of extended storage life after harvest and prior to processing. Thus, the canner can defer processing of 'Rizzi' until completion of the processing of other late clingstone peach varieties which lack 'Rizzi's' storage life capacity. In this connection, the potential storage period of 'Rizzi' before canning is about eight weeks making it superior to most other clingstone peaches when quality factors such as skin color, flesh color, firmness, soluble solids content, pH and titratable acidity are taken into account.

BOTANICAL DESCRIPTION

The following description of 'Rizzi' was developed from fruit and plant material obtained in the second week of September 1990. The fruit is described at full commercial maturity. Color definitions used below are from "Dictionary of Color" by Maerz and Paul, published in 1950.

TREE DESCRIPTION

Form: Medium in size and upright to upright-spreading in form. The tree is vigorous and productive. The tree is hardy under typical California interior valley climatic conditions.

Branches: Average in caliper and surface texture. Shoots from current season's growth a light green in color (18-H-6). Surfaces of current season's growth exposed to direct sunlight are tinged with reddish-brown.

Leaves: Leaf measurements have been taken from leaves growing on shoots of medium vigor located on the periphery of the tree. Average leaf length 14.3 cm including the petiole. Average leaf width 2.9 cm.

*Leaf form.*—Form is linear lanceolate. Leaf apex is acuminate with the tip distinctly curved downwards.

*Leaf color.*—Upper leaf surface a dark green (22-L-8). Color of underside of leaf a lighter green (21-J-8). Midvein on lower leaf surface a pale green-yellow (19-J-5).

*Leaf margin.*—Margin form crenate. The crenations are well defined and regular. Most crenationse tipped with a dark brown trichome. The leaf margins are moderately undulate.

*Leaf petiole.*—Petiole length moderately long ranging from 8.0 to 9.0 mm. Petiole thickness averages 1.0 mm. Petiole color is a light green (19-K-6).

*Leaf glands.*—The glands are very small in size and mixed in form, with both reniform and globose types present. One to three glands are present on the petiole. These petiole glands are usually reinform in shape and located just below the basal leaf margin. An additional four to six glands are present upon the basal leaf margin and are predominately globose in shape and very small in size. Gland color is a shiny yellow to yellow-green (17-K-2). Gland position is alternate.

FRUIT DESCRIPTION

Maturity: This new clingstone peach cultivar is classified in the "Late" maturity group. Fruit ripens after the 'Ross' cultivar and slightly before the 'Dr. Davis' cultivar in about the third week of August.

Fruit size: Uniform and of medium size. Average cheek diameter 68.2 mm, average suture diameter 66.0 mm, average axial diameter 63.2 mm.

Fruit form: In lateral aspect the fruit is globose to slightly oblate in form. In apical aspect the fruit is nearly globose with slight variability.

Fruit suture: The ventral suture is a fine line from base to apex, but less distinct over the apical shoulder. A slight amount of stitching is evident along the suture. A suture groove is also evident on the dorsal side of the fruit. Some red coloration can be associated with the suture on the more highly blushed fruit.

Ventral surface: Usually quite smooth with no lipping.

Stem cavity: Broad and moderately deep. Average length 3.3 cm, average width 2.4 cm, average depth 1.8 cm.

Fruit base: Rounded to slightly truncate in form. Base angle slightly variable but most often at right angle to fruit axes.

Fruit apex: The apex is generally rounded with the tip somewhat depressed. The pistil point is variable but usually is oblique. There is a distinct depression on both the dorsal and ventral side of the apex.

Fruit stem: Medium in length averaging 1.1 cm. Medium in thickness averaging 0.3 cm.

Fruit skin: Pubescent with a fine, short, matted pubescence. No observed tendency to crack.

Skin color: The primary ground color is a uniform orange-yellow (10-K-7). The fruit surface has a moderate amount of blush coloration present, from 20 to 60 percent of the total surface. Fruit exposed to direct sunlight are usually in the highest percent category. The blush pattern is primarily washed with a moderate amount of dark mottling present. The blush color ranges from a dark garnet red (8-J-6) to a lighter shade of red (6-L-7) with a range of variation in between.

Flesh color: A uniform yellow from skin to stone cavity (10-K-5).

Flesh texture: Fine and non-melting.

Flesh fibers: Few in number, short and fine.

Ripening: Ripens evenly.

Flavor: High quality.

Aroma: Moderate, pleasant.

STONE DESCRIPTION

Attachment: Full clingstone.

Stone size: Medium to smaller than average. Average length 28.3 mm, average width 22.0 mm, average thickness 17.0 mm.

Fibers: Numerous very short and fine fibers present, attached laterally to the stone.

Form: Variable but most often slightly obovate.

Base: Slightly truncate in form. Base angle oblique to the stone axis.

Hilum: Medium in size and well defined. Hilum form oval.

Apex: Apex form is generally rounded with a broad, rather blunt tip.

Stone side: Variable but most often nearly equal.

Stone surface: Moderately coarse with the heaviest grooving apically over the lateral apical shoulders and basally over the lateral basal shoulder. Several deep grooves are present near the ventral suture running nearly parallel to the suture. The sides of the stone are pitted at mid-stone laterally.

Ventral edge: Medium in width with several low wings converging apically.

Dorsal edge: Somewhat variable in form, but most often the dorsal suture is moderately narrow with a deep groove present from base up to the apical shoulder. The apical shoulder area is substantially eroded and essentially concave in shape. The dorsal groove is bordered by two high ridges which can be continuous or can be cut in two to four places by cross grooves.

Stone color: The color of the dry stone is a light buff-brown (13-B-14).

Tendency to split: No tendency observed.

FLORAL DESCRIPTION

Bloom timing: Average in time of bloom in relation to other commercial cling peach cultivars. Date of full bloom at Winters, Calif., Feb. 24, in 1991.

Flower size: Small, non-showy in form. Average flower diameter 22 mm when fully expanded.

Bloom quantity: Abundant, most commonly two flowers per node.

Flower buds and scales: Bud scale color a medium brown (Rustic brown (7-H-11). Buds of medium size and conic in shape. Bud scales heavily pubescent.

Flower petals: Broadly oval in form average length 11 mm, average width 8.5 mm. Petal color a very light pink in the central area of the petal (1-B-1) and a dark pink along the outer margin (1-E-2). The petal claw is relatively narrow and truncate. Claw color a dark pink (1-G-2). Petal margins are moderately undulate and the petals are substantially cupped inward. The petal apices are usually rounded with no tip. Petal number is five.

Flower pedicel: Relatively short, from 1 to 1.5 mm in length. Average thickness, 1.0 mm. Pedicel color a light green (18-I-7). Pedicel surface glabrous.

Nectaries: Color a moderately bright orange (11-J-11).

Anthers: Average in size. Anther color tan ventrally (Chamois 11-I-5), red in color dorsally (Brick-dust 5-L-11).

Pollen: Abundant. Pollen color a bright yellow (Empire yellow 9-K-3).

Stamens: Medium length, slightly longer than the pistil at full maturity. Filament color nearly white when the bloom first opens, darkening to a dull light violet with senescence (4-H-3).

Pistil: Pistil length average 16 mm including ovary. Pistil color is a light yellow-green (17-J-2). The pistil surface is highly pubescent.

FRUIT USE

The new cultivar described above is a non-melting clingstone peach in the "Late" maturity group, ripening in mid-August. The new fruit ripens after the 'Ross' cultivar and before the 'Dr. Davis' cultivar. This new cultivar would be utilized in the canning and fruit processing industries.

We claim:

1. We claim the new and distinct variety of clingstone peach tree illustrated and described and having the characteristics above enumerated.

* * * * *